US00PP08382P

United States Patent [19]

Klemm

[11] Patent Number: Plant 8,382

[45] **Date of Patent: * Sep. 21, 1993**

[54] GERANIUM PLANT NAMED KLEPELWA

[75] Inventor: Siegfried Klemm, Stuttgart, Fed. Rep. of Germany

[73] Assignee: Selecta Klemm, Stuttgart, Fed. Rep. of Germany

[ * ] Notice: The portion of the term of this patent subsequent to Jun. 21, 2008 has been disclaimed.

[21] Appl. No.: 450,582

[22] Filed: Dec. 14, 1989

[51] Int. Cl.[5] ..... A01H 5/00

[52] U.S. Cl. ..... Plt./87.12

[58] Field of Search ..... Plt./68

*Primary Examiner*—Howard J. Locker

[57] ABSTRACT

A new and distinct variety of *Pelargonium peltatum* which is particularly distinguished by the soft Phlox Pink color which floods from the closely massed clusters of the flowers and covers the plants like a veil due to the many flowers and the graceful growth of the plant. Each of the flowers has as many as nine florets, the petals of which have a Spirea Red center portion radiating outwardly over a major portion of the petal body with a Light Pink color which in the mass of the flowers presents an overall Phlox Pink coloration. In this new variety, each of the flowers, with its many florets, forms a loose cluster held in a mass above the intensive green color of the foliage by means of a strong stalk having a length of 12 to 13 cm.

No Drawings

BACKGROUND OF THE NEW PLANT

This new geranium variety was discovered as a sport of an unnamed, unpatented, proprietary variety among a greenhouse collection of miscellaneous geranium varieties, maintained primarily for use as breeding material. This newly discovered plant was propagated by cuttings with such satisfactory results that propagation under controlled conditions was continued for as long as five years to make certain that its homogeneity can be assured for sale over a wide market.

DESCRIPTION OF THE DRAWING

The accompanying full-color photographic drawing illustrates the form and floral display of the cultivar as well as the nature of its blooms and buds.

DESCRIPTION OF THE NEW VARIETY

The following is a detailed description of my new variety of geranium plant as observed from greenhouse grown plants at Stuttgart, West Germany with color designations according to The R.H.S. Colour Chart published by The Royal Horticultural Society of London, England. The colors shown are as nearly true to those herein specified as is reasonably possible to obtain by conventional photographic procedures.

THE PLANT

Origin: Sport of an unnamed, unpatented variety.
Parentage: Unknown.
Classification:
*Botanic.*—*Pelargonium peltatum* Hybrid.
*Commercial.*—Ivy geranium.
Form: Hanging bush, having a shape like ivy.
Growing rate: Medium.
Branching character:
*Tendrils.*—About 40 cm. long.
Growth habit: Vigorous and spreading.
Strength: Very good.
Foliage:

*Quantity.*—Abundant.
*Shape of leaf.*—Like ivy with entire margins.
*Size.*—Medium to small.
*Texture.*—Glossy.
*Color.*—Upper side — Green with small zonation. Under side — Lighter green.
*Ribs and veins.*—5 or 6 main veins on each leaf.

INFLORESENCE

Blooming habit: Continuous and profusely from Spring to late Fall.
Size of flower: Medium.
*Diameter.*—In average about 4 cm.
Borne: On a strong upright stalk.
Florets:
*Number.*—Average about 9.
Petalage:
*Number.*—8 to 12.
*Form.*—Oboviate with entire margins.
*Persistance*—Petals stay on stem 4 to 5 days.
*Texture.*—Soft.
*Appearance.*—Satiny.
*Color.*—Generally Phlox Pink 62-B with Spiraea Red 63-C at the base portion of the petal.
Flower stem:
*Length.*—About 10 cm.
*Color.*—Green.
Persistence: The petals fall down when the flower is old.
Lasting quality: Long lasting on the plant, like all ivys.

THE BUD

Size: Small.
*Diameter.*—About 10 mm.
*Length.*—About 12 to 14 mm.
Shape: Elliptic and pointed.
Opening rate: Medium.
Colors of petals:
*When sepals first divide.*—White to Light Pink.
*When petals begin to unfurl.*—Light Pink.
Sepals:
*Number.*—Five.

*Shape.*—Ellipical.
*Character.*—The sepals stand up when the florets open.
*Color.*—Inside and outside — Green.

Calyx:
*Shape.*—Broad.
*Aspect.*—Hairy.
*Splitting.*—Calyx does not split.

THE REPRODUCTIVE ORGANS

Stamens:
*Number.*—7.
*Arrangement.*—Sometimes 5 long and 2 short around the ovaries.

Anthers:
*Size.*—1.3 mm.
*Color.*—Orange Red.

Filaments:
*Length.*—About 5 to 7 mm.

Pollen:
*Color.*—Orange.

Pistils:
*Number.*—1.
*Styles.*—Length: About 5 mm.

Fruit:
*Fertility.*—The fruit is fertile.
*Shape.*—Ovoid.
*Color at maturity.*—Light Brown.

This new variety most nearly resembles the variety Lachskonigin due to its earliness and rich flowering. The new variety differs however in that the flowers are smaller, the flower stem and the clusters are more graceful and the new variety blooms very early and is very floriferous. Although the present plant is an ivy geranium, often called a hanging plant, this plant grows like a normal geranium and later the branches are hanging over the pot. During the Summer, the branches are growing larger, therefore, this type of geranium is very suitable for hanging baskets.

I claim:

1. The new and distinct variety of geranium plant substantially as herein shown and described and particularly characterized by its early and rich flowering with a profuse and continuous production of flowers having a generally Phlox Pink color which extends in a uniform manner over the entire extent of the blooming plant.

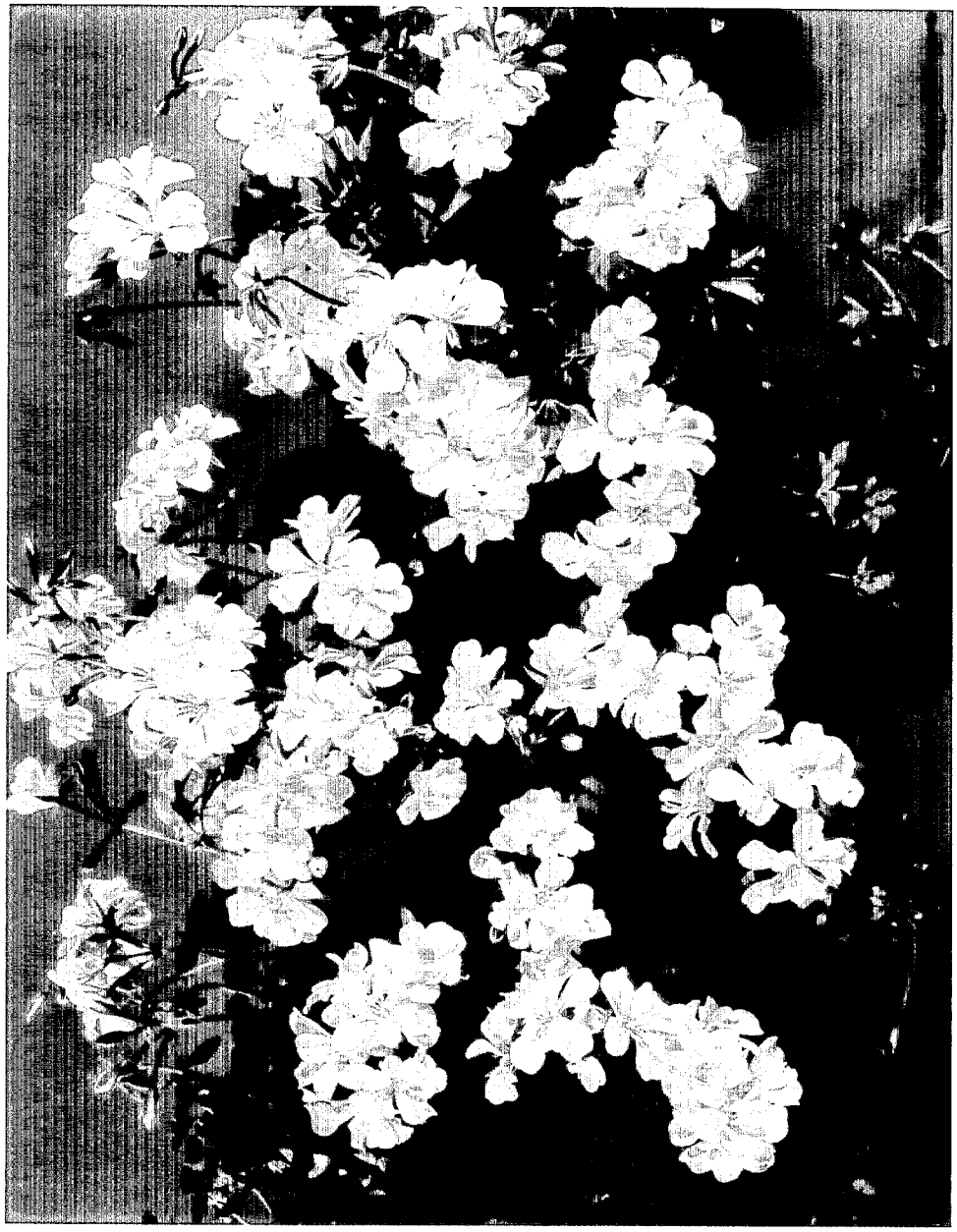

* * * * *